(12) United States Patent
Cheng et al.

(10) Patent No.: US 9,018,418 B2
(45) Date of Patent: Apr. 28, 2015

(54) METHOD FOR PREPARATION OF ARYL POLY(OXALKYL) QUATERNARY AMMONIUM COMPOUND

(75) Inventors: Che Jim Cheng, Beijing (CN); Fei Song, Beijing (CN); Yongmei Pan, Beijing (CN)

(73) Assignee: Beijing Sunpu Biochem. Tech. Co., Ltd., Beijing (CN)

( * ) Notice: Subject to any disclaimer, the term of this patent is extended or adjusted under 35 U.S.C. 154(b) by 0 days.

(21) Appl. No.: 14/003,200

(22) PCT Filed: Jan. 17, 2012

(86) PCT No.: PCT/CN2012/070457
§ 371 (c)(1),
(2), (4) Date: Sep. 4, 2013

(87) PCT Pub. No.: WO2013/040869
PCT Pub. Date: Mar. 28, 2013

(65) Prior Publication Data
US 2014/0187819 A1    Jul. 3, 2014

(30) Foreign Application Priority Data
Sep. 19, 2011  (CN) .......................... 2011 1 0278338

(51) Int. Cl.
| | | |
|---|---|---|
| C07C 213/08 | (2006.01) | |
| C07C 213/02 | (2006.01) | |
| C07C 217/08 | (2006.01) | |
| C07C 41/16 | (2006.01) | |

(52) U.S. Cl.
CPC ............. *C07C 213/08* (2013.01); *C07C 213/02* (2013.01); *C07C 217/08* (2013.01); *C07C 41/16* (2013.01)

(58) Field of Classification Search
CPC ........................... C07C 213/10; C07C 213/06
See application file for complete search history.

(56) References Cited

U.S. PATENT DOCUMENTS

| | | |
|---|---|---|
| 2,115,250 A | 4/1938 | Bruson |
| 2,170,111 A | 8/1939 | Bruson |
| 2,229,024 A | 1/1941 | Bruson |
| 2,406,902 A | 9/1946 | Rawlins |
| 2,547,144 A | 4/1951 | Whiting |
| 2,608,584 A | 8/1952 | Sprules et al. |
| 2,706,142 A | 4/1955 | Von Glahn et al. |
| 3,244,589 A | 4/1966 | Sunnen et al. |
| 6,794,543 B2 | 9/2004 | Raab et al. |
| 7,109,161 B1 | 9/2006 | Gayed |
| 7,342,044 B2 | 3/2008 | Lutz |
| 2003/0114533 A1* | 6/2003 | Raab et al. .................. 514/643 |
| 2006/0106024 A1 | 5/2006 | Levy et al. |

FOREIGN PATENT DOCUMENTS

| | | |
|---|---|---|
| CN | 1371287 A | 9/2002 |
| CN | 1281129 C | 10/2006 |
| EP | 1 892 235 A1 | 2/2008 |
| WO | WO 01/07086 A1 | 2/2001 |

OTHER PUBLICATIONS

Chu, "Synthesis and evaluation of isatin analogs as caspase-3 inhibitors: Introduction of a hydrophilic group increases potency in a whole cell assay," *Bioorganic & Medicinal Chemistry Letters*, 21: 2192-2197 (2011).

Liang et al., "Novel method for synthesis of β-(β'-chloroethoxyl)phenetole," *Chemistry*, No. 2, pp. 38-39 (1994).

Yagi et al., "Colorimetric sensing of metal ions by bis(spiropyran) podands: Towards naked-eye detection of alkaline earth metal ions," *Dyes and Pigments*, 80: 98-105 (2009).

International Search Report mailed Jun. 21, 2012, for International Application No. PCT/CN12/70457.

* cited by examiner

*Primary Examiner* — Sudhakar Katakam
*Assistant Examiner* — Jennifer C Sawyer
(74) *Attorney, Agent, or Firm* — Kilyk & Bowersox, P.L.L.C.

(57) ABSTRACT

A method for preparation of an aryl poly(oxalkyl) quaternary ammonium compound is provided, said method comprising steps of: 1) reacting a phenol with a dihalopolyalkylene ether under the action of a phase transfer catalyst, to obtain an arylpoly(oxalkyl) halide; 2) reacting said arylpoly(oxalkyl) halide with an amination reagent under the action of a phase transfer catalyst, to obtain an arylpoly(oxalkyl) amine; 3) reacting said arylpoly(oxalkyl) amine with an alkylation reagent, to obtain an aryl poly(oxalkyl) quaternary ammonium compound; wherein $R_1$ is H or a $C_1$ to $C_{16}$ alkyl group, located in the ortho, meta or para position; n is an integer of 2 to 6; $R_2$ is H or a $C_1$ to $C_{16}$ alkyl group; $R_3$ is H or a $C_1$ to $C_{16}$ alkyl group; $R_4$ is a $C_1$ to $C_{16}$ alkyl group; $X_1$ is Br or Cl; X is Cl, Br, or I. The preparation method according to the present invention requires low temperature and low pressure, the reaction time is short, and an overall yield can reach 75%. The operation is simple, the cost is low, and the product can be separated easily and have a purity of pharmaceutical grade, thereby facilitating the large-scale production.

20 Claims, No Drawings

METHOD FOR PREPARATION OF ARYL POLY(OXALKYL) QUATERNARY AMMONIUM COMPOUND

The present application claims from the benefit of Chinese patent application No. 201110278338.X, filed in the SIPO on Sep. 19, 2011 and titled "Method for Preparation of Aryl poly(oxalkyl) quaternary ammonium Compound," the entire disclosure of which is incorporated herein by reference.

TECHNICAL FIELD

The present invention relates to the compound synthesis field, and particularly relates to a method for preparation of an aryl poly(oxalkyl) quaternary ammonium compound.

BACKGROUND ART

For a long time, arylpoly(oxalkyl) quaternary ammonium substances have been used as wetting agents, emulsifying agents, dispersing agents and detergents because of their excellent properties. Because of their bactericidal and antifungal activities, these surface-active substances are widely used as cosmetic antiseptic, sanitizer and fungicide used in dairy and food enterprises, clinical reagents and pharmaceutical aids for measuring the protein content. A typical substance is benzethonium chloride. It has a broad-spectrum microbe-killing effect and is stable within comparatively wide pH and temperature ranges. Thus, it is widely used in a variety of products for sterilization, disinfection, sanitation and washing of equipment, etc. In addition, it also has a very broad prospect in cosmetic additives application.

U.S. Pat. Nos. 2,115,250 and 2,229,024 provide methods for preparing relevant substances. According to the prior art, arylpoly(oxalkyl) amine substances are usually prepared by reacting equimolar quantity of a phenol and a dihalopolyalkylene ether under reflux in an alkaline condition. The resultant product then reacts with an amination reagent. After the completion of the reaction, amine hydrohalide is neutralized by a hydroxide of an alkaline earth metal. According to this method, reactions in both steps involve high temperature and comparatively long reaction time, and have rigorous requirements on the temperature resistance and pressure resistance of the equipment.

U.S. Pat. No. 6,794,543 provides a process for preparing aryl poly(oxalkyl)benzyl-dimethylammonium derivatives by reaction of aryl poly(oxalkyl) halides with benzyl dimethylamine or substituted benzyl dimethylamine in a suitable solvent. Although it is declared by this invention that the preparation process is simplified, the practical application also relates to the preparation of the used raw material—aryl poly(oxalkyl) halides. Moreover, collection and purification of the resultant quaternary ammonium substances are too complicate, and there are also problems relating to long reaction time under high temperature, and temperature resistance and pressure resistance of the reaction equipment.

SUMMARY OF THE INVENTION

The problem to be solved by the present invention is to provide a method for preparation of an aryl poly(oxalkyl) quaternary ammonium compound, of which the operations are simple with a low requirement on the reaction conditions.

To solve the above-mentioned technical problems, the technical solution of the present invention is as follows:

A method for preparation of an aryl poly(oxalkyl) quaternary ammonium compound, said method comprising steps of:

1) reacting a phenol represented by formula (a) with a dihalopolyalkylene ether represented by formula (b) under the action of a phase transfer catalyst, to obtain an arylpoly (oxalkyl) halide represented by formula (c);

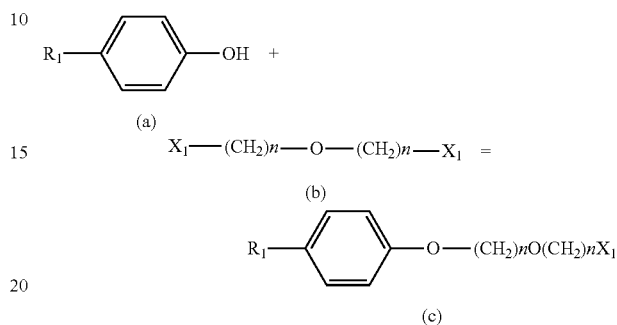

2) reacting said arylpoly(oxalkyl) halide with an amination reagent under the action of a phase transfer catalyst, to obtain an arylpoly(oxalkyl) amine represented by formula (d);

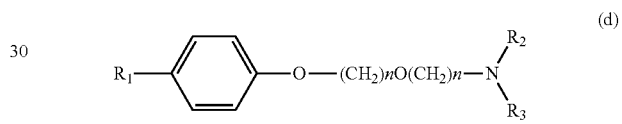

3) reacting said arylpoly(oxalkyl) amine with an alkylation reagent, to obtain an aryl poly(oxalkyl) quaternary ammonium compound represented by formula (e);

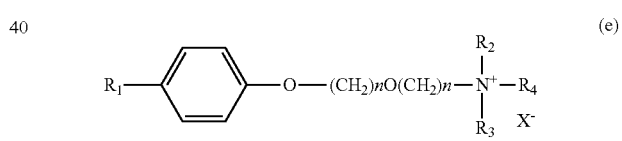

wherein, $R_1$ is H or a $C_1$ to $C_{16}$ alkyl group, located in the ortho, meta or para position; n is an integer of 2 to 6; $R_2$ is H or a $C_1$ to $C_{16}$ alkyl group; $R_3$ is H or a $C_1$ to $C_{16}$ alkyl group; $R_4$ is a $C_1$ to $C_{16}$ alkyl group; $X_1$ is Br or Cl; X is Cl, Br, or I.

Preferably, $R_1$ is a $C_4$ to $C_{10}$ alkyl group, $R_2$ is a $C_1$ to $C_6$ alkyl group, $R_3$ is a $C_1$ to $C_6$ alkyl group.

Preferably, said phenol is one of phenol, cresol, 5-methyl-2-isopropyl phenol, 2-methyl-5-isopropyl phenol, p-tert-butyl phenol, p-sec-butyl phenol, p-tert-pentyl cresol, p-sec-octyl phenol or p-tert-octyl phenol; and said dihalopolyalkylene ether is one of β,β'-dichloro diethyl ether, β,β'-dichloro diisopropyl ether, β,β'-dichloro dibutyl ether, β,β'-dichloro dipentyl ether, β,β'-dibromo diethyl ether, β,β'-dibromo diisopropyl ether, β,β'-dibromo dibutyl ether, β,β'-dibromo dipentyl ether.

Preferably, in step 1) a molar ratio between said phenol and said dihalopolyalkylene ether is 1:1.0 to 1:10.

Preferably, said phase transfer catalyst in steps 1) and 2) is one or more of a quaternary ammonium salt, a quaternary phosphonium salt, a polyether compound, or a cyclic crown ether compound.

Preferably, the amount of said phase transfer catalyst in step 1) is 1% to 50% of the mole number of said phenol; and the amount of said phase transfer catalyst in step 2) is 1% to 50% of the mole number of said arylpoly(oxalkyl) halide.

Preferably, the chemical formula of said quaternary ammonium salt is formula (f), and the chemical formula of said quaternary phosphonium salt is formula (g):

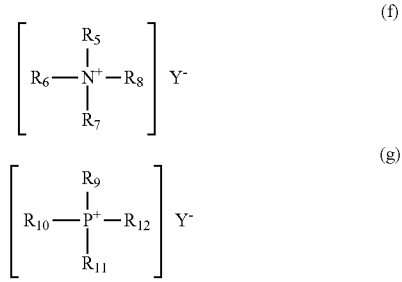

wherein each of $R_5$, $R_6$, $R_7$, $R_8$ is a $C_2$ to $C_8$ alkyl group; and each of $R_9$, $R_{10}$, $R_{11}$, $R_{12}$ is a $C_2$ to $C_8$ alkyl group;

$Y^-$ is $HSO_4^-$, $Br^-$ or $Cl^-$.

Preferably, said quaternary ammonium salt is a tetraalkyl ammonium salt or a benzyl trialkyl ammonium salt; and said quaternary phosphonium salt is a tetraalkyl phosphonium salt or a benzyl trialkyl phosphonium salt.

Preferably, said quaternary ammonium salt is one or more of benzyl triethyl ammonium chloride, tetrabutyl ammonium chloride, tetrabutyl ammonium bromide, tetrabutyl ammonium sulfate; said quaternary phosphonium salt is methyl triphenyl phosphonium bromide; said polyether compound is one or both of a chain-like polyethylene glycol or polyethylene glycol dialkyl ethers; and said cyclic crown ether compound is one or more of 18-crown-6, 15-crown-5, cyclodextrin compound.

Preferably, step 1) is carried out in an alkaline condition. The alkali being added is one or more of sodium amide, sodium methoxide, sodium hydroxide, potassium hydroxide, potassium carbonate. A molar ratio between said alkali and said phenol is 1:1.0 to 1:5.0.

Preferably, in step 1), the reaction temperature is 40° C. to 250° C., and the reaction time is 1 hour to 72 hours.

Preferably, step 1) is carried out in organic solvent, said organic solvent is one or more of dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, butanone, methyl isobutyl ketone, methyl n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

Preferably, said amination reagent in step 2) is one of ammonia, methylamine, dimethylamine, ethylamine, diethylamine, monoethanolamine, diethanolamine, dibenzylamine, cyclohexylamine, piperidine, morpholine.

Preferably, in step 2), a molar ratio between said arylpoly(oxalkyl) halide and said amination reagent is 1:1.0 to 1:12.0.

Preferably, in step 2), the reaction temperature is 40° C. to 200° C., and the reaction time is 1 hour to 48 hours.

Preferably, said alkylation reagent in step 3) is one of benzyl chloride, benzyl bromide, p-methoxybenzyl chloride, 2-methyl-1-allyl chloride, iodomethane, bromoethane.

Preferably, in step 3), a molar ratio between said arylpoly(oxalkyl) amine and said alkylation reagent is 1:1 to 1:10.

Preferably, in step 3), the reaction temperature is 40° C. to 250° C., and the reaction time is 1 hour to 48 hours.

Preferably, step 3) is carried out in organic solvent, said organic solvent is halogenated hydrocarbons, ketones, ethers containing from 2 to 8 carbon atoms and aromatic hydrocarbons, specifically, one or more of butanone, methyl isobutyl ketone, methyl-n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

Preferably, a crystallization solvent is used in step 3), said crystallization solvent is one or more of carbon disulfide, isopropyl ether, petroleum ether, cyclohexane.

During the process of preparing the aryl poly(oxalkyl) quaternary ammonium compound in the present invention, a phase transfer catalyst is used, which can obviously decrease temperature and pressure of the reaction system, reduce the reaction time. An overall yield of the reaction can be increased to 75%, the operation is simple, the cost is low, and the product can be separated easily and have a purity of pharmaceutical grade, thereby facilitating the large-scale production.

DESCRIPTION OF PREFERRED EMBODIMENTS

To further understand the present invention, the following preferred embodiments of the present invention will be described in combination with examples. But it should be understood that these descriptions are merely to further illustrate the features and advantages of the present invention, rather than a limitation to the claims of the present invention.

The present invention provides a method for preparation of an aryl poly(oxalkyl) quaternary ammonium compound, said method comprising steps of:

1) reacting a phenol represented by formula (a) with a dihalopolyalkylene ether represented by formula (b) under the action of a phase transfer catalyst, to obtain an arylpoly(oxalkyl) halide represented by formula (c);

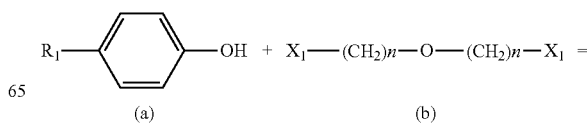

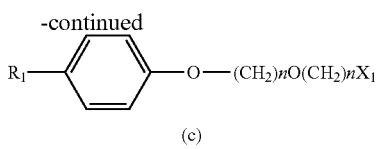

(c)

wherein, $R_1$ is H or a straight or branched $C_1$ to $C_{16}$ alkyl group, located in the ortho, meta or para position; n is an integer of 2 to 6; $X_1$ is Br or Cl.

Said phenol can be one of phenol, cresol, 5-methyl-2-isopropyl phenol, 2-methyl-5-isopropyl phenol, p-tert-butyl phenol, p-sec-butyl phenol, p-tert-pentyl cresol, p-sec-octyl phenol or p-tert-octyl phenol; and said dihalopolyalkylene ether can be one of β,β'-dichloro diethyl ether, β,β'-dichloro diisopropyl ether, β,β'-dichloro dibutyl ether, β,β'-dichloro dipentyl ether, β,β'-dibromo diethyl ether, β,β'-dibromo diisopropyl ether, β,β'-dibromo dibutyl ether, β,β'-dibromo dipentyl ether.

A molar ratio between said phenol and said dihalopolyalkylene ether is 1:1 to 1:10, more preferably 1:1.5 to 1:5.5.

Said phase transfer catalyst used in the reaction is one or more of a quaternary ammonium salt, a quaternary phosphonium salt, a polyether compound, or a cyclic crown ether compound, and the amount of said phase transfer catalyst is 1% to 50% of the mole number of said phenol.

The chemical formula of said quaternary ammonium salt is formula (f), and the chemical formula of said quaternary phosphonium salt is formula (g):

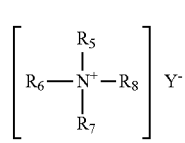

(f)

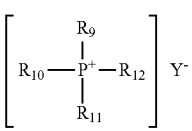

(g)

wherein each of $R_5$, $R_6$, $R_7$, $R_8$ is a $C_2$ to $C_8$ alkyl group, which can be identical or different groups; each of $R_9$, $R_{10}$, $R_{11}$, $R_{12}$ is a $C_2$ to $C_8$ alkyl group, which can be identical or different group; and $Y^-$ is $HSO_4^-$, $Br^-$ or $Cl^-$.

Said quaternary ammonium salt is preferably a tetraalkyl ammonium salt or a benzyl trialkyl ammonium salt, more preferably one or more of benzyl triethyl ammonium chloride, tetrabutyl ammonium chloride, tetrabutyl ammonium bromide, tetrabutyl ammonium sulfate; and said quaternary phosphonium salt is preferably a tetraalkyl phosphonium salt or a benzyl trialkyl phosphonium salt, more preferably methyl triphenyl phosphonium bromide.

Further, said polyether compound is one or both of a chain-like polyethylene glycol or polyethylene glycol dialkyl ethers; and said cyclic crown ether compound is preferably one or more of 18-crown-6, 15-crown-5, cyclodextrin compound.

It is preferable that the reaction is carried out in an alkaline condition. The alkali being added is one or more of sodium amide, sodium methoxide, sodium hydroxide, potassium hydroxide, potassium carbonate. A molar ratio between said alkali and said phenol is 1:1.0 to 1:5.0.

Preferably, the reaction temperature is 40° C. to 250° C., and the reaction time is 1 hour to 72 hours.

It is preferable that the reaction is carried out in an organic solvent which does not react with the phenol, the dihalopolyalkylene ether and the phase transfer catalyst. The organic solvent can be one or more of dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, butanone, methyl isobutyl ketone, methyl n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

The yield in this reaction step can reach 88% or higher.

2) Reacting the obtained arylpoly(oxalkyl) halide with an amination reagent under the action of a phase transfer catalyst, to obtain an arylpoly(oxalkyl) amine represented by formula (d);

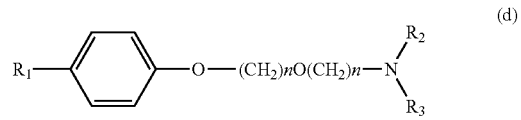

(d)

$R_2$ is H or a $C_1$ to $C_{16}$ alkyl group; $R_3$ is H or a $C_1$ to $C_{16}$ alkyl group.

Said amination reagent can be selected from ammonia, primary amine, secondary amine. Specifically, it can be one of ammonia, methylamine, dimethylamine, ethylamine, diethylamine, monoethanolamine, diethanolamine, dibenzylamine, cyclohexylamine, piperidine, morpholine.

Preferably, a molar ratio between said arylpoly(oxalkyl) halide and said amination reagent is 1:1.0 to 1:12.0, more preferably 1:2.0 to 1:6.0.

In this step, the reaction temperature is 40° C. to 200° C., and the reaction time is 1 hour to 48 hours.

The yield in this reaction step can reach 90% or higher.

3) Reacting said arylpoly(oxalkyl) amine with an alkylation reagent, to obtain an aryl poly(oxalkyl) quaternary ammonium compound represented by formula (e);

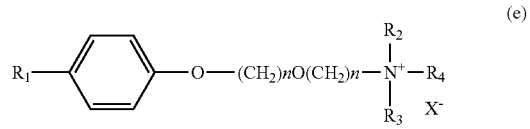

(e)

$R_4$ is a $C_1$ to $C_{16}$ alkyl group; X is Cl, Br, or I.

Said alkylation reagent is an alkyl halide. It is preferably one of benzyl chloride, benzyl bromide, p-methoxybenzyl chloride, 2-methyl-1-allyl chloride, iodomethane, bromoethane.

Preferably, a molar ratio between said arylpoly(oxalkyl) amine and said alkylation reagent is 1:1 to 1:10.

In this step, the reaction temperature is 40° C. to 250° C., and the reaction time is 1 hour to 48 hours.

Preferably, step 3) is carried out in an organic solvent having a slightly strong polarity. The organic solvent is halogenated hydrocarbons, ketones, ethers containing from 2 to 8 carbon atoms and aromatic hydrocarbons, specifically, it can be one or more of butanone, methyl isobutyl ketone, methyl-n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

This reaction uses a crystallization solvent to carry out crystallization. The crystallization solvent is one or more of carbon disulfide, isopropyl ether, petroleum ether, cyclohexane etc., which are solvents having a slightly weak polarity. The yield in this reaction step can reach 95% or higher.

Example 1

8.4 g of benzyl triethyl ammonium chloride, 143.0 g of β,β'-dichloro diethyl ether, 225.0 g of toluene were added to a 1 L four-necked reaction flask in which 103.0 g of p-(α,α,γ,γ-tetramethylbutyl) phenol was added. The reaction mixture was heated to 110° C. to reflux. 105.0 g of sodium hydroxide solution having a concentration of 20% was slowly dropwise added. The reflux was maintained for 5 hours after the completion of the dropwise addition. The supernatant organic phase was subjected to gas chromatography detection, which showed a conversion rate of 99.7% of p-tert-octyl phenol. The reaction solution was separated to remove aqueous phase. The organic phase was distilled under reduced pressure to separately recover toluene and excess β,β'-dichloro diethyl ether. The distillation residue was about 144.6 g of a yellow viscous liquid. Gas chromatography detection showed that the content of p-tert-octyl phenoxy ethoxy ethyl chloride was 96.8%.

The above product was added to a 0.5 L sealable reactor, to which were added 11.4 g of benzyl triethyl ammonium chloride and 135.3 g of aqueous dimethylamine solution having a concentration of 33%. The reactor was sealed and warmed to 160° C. The reaction was carried out under stirring for 3 hours. The reaction solution was separated to remove aqueous phase. 138.2 g of organic phase was collected. Gas chromatography detection showed that the conversion rate of p-tert-octyl phenoxy ethoxy ethyl dimethylamine was 100%, and the content thereof after concentration was 97.8%.

The above obtained p-tert-octyl phenoxy ethoxy ethyl dimethylamine was added to a 1 L four-necked reaction flask, to which were sequentially added 100.2 g of methyl isobutyl ketone and 126.6 g of benzyl chloride. The flask was heated to reflux. The reaction was carried out for 2 hours. Then, 168.2 g of cyclohexane was added slowly. The flask was cooled to carry out crystallization. 172.7 g of a white solid was collected, to obtain benzethonium chloride. The content of benzethonium chloride was 99.2% determined by titration according to the method described on page 247 of the United States Pharmacopeia USP29. The measured melting point was from 159.0 to 160.1° C. As calculated with reference to p-tert-octyl phenol, an overall yield of the three steps was 77.5%.

Example 2

15.5 g of methyl triphenylphosphonium bromide, 590.0 g of β,β'-dichloro diethyl ether, 225.0 g of N,N-dimethyl formamide were added to a 1 L four-necked reaction flask in which 96.0 g of p-(α,α,γ,γ-tetramethylbutyl) phenol was added. The reaction mixture was heated to reflux. 130.0 g of potassium hydroxide solution having a concentration of 20% was slowly dropwise added. The reflux was maintained for 20 hours after the completion of the dropwise addition. The supernatant organic phase was subjected to gas chromatography detection, which showed a conversion rate of 99.0% of p-tert-octyl phenol. The reaction solution was separated to remove aqueous phase. The organic phase was distilled under reduced pressure to separately recover methyl isobutyl ketone and excess β,β'-dichloro diethyl ether. The distillation residue was about 176.2 g of a yellow viscous liquid. Gas chromatography detection showed that the content of p-tert-octyl phenoxy ethoxy ethyl chloride was 95.0%.

The above product was added to a 1 L sealable reactor, to which were added 7.8 g of methyl triphenylphosphonium bromide and 52.0 g of aqueous dimethylamine solution having a concentration of 40%. The reactor was sealed and warmed to 46° C. The reaction was carried out under stirring for 48 hours. The reaction solution was separated to remove aqueous phase. 124.8 g of organic phase was collected. Gas chromatography detection showed that the conversion rate of p-tert-octyl phenoxy ethoxy ethyl dimethylamine was 100%, and the content thereof after concentration was 94.7%.

The above obtained p-tert-octyl phenoxy ethoxy ethyl dimethylamine was added to a 1 L four-necked reaction flask, to which were sequentially added 100.0 g of tetrahydrofuran and 73.0 g of p-methoxy benzyl chloride. The flask was heated to 45° C. The reaction was carried out for 45 hours. Then, 150.0 g of petroleum ether was added slowly. The flask was cooled to carry out crystallization. 156.0 g of a white solid was collected, to obtain benzethonium chloride. The content thereof was 99.6% determined by titration. As calculated with reference to p-tert-octyl phenol, an overall yield of the three steps was 75.1%.

Example 3

9.8 g of tetrabutylammonium bromide, 400.0 g of β,β'-dibromo diethyl ether and 150.0 g of N-methylpyrrolidone were sequentially added to a 1 L four-necked reaction flask in which 51.5 g of p-(α,α,γ,γ-tetramethylbutyl) phenol was added. The reaction mixture was heated to 205° C. to reflux. 98.0 g of potassium hydroxide solution having a concentration of 15% was slowly dropwise added. The reflux was maintained for 8 hours after the completion of the dropwise addition. The reaction solution was separated to remove aqueous phase. The organic phase was distilled under reduced pressure to separately recover methyl isobutyl ketone and excess β,β'-dibromo diethyl ether. The distillation residue was about 93.0 g of a yellow viscous liquid. Gas chromatography detection showed that the content of p-tert-octyl phenoxy ethoxy ethyl bromide was 95.6%.

The above product was added to a 0.5 L sealable reactor, to which were added 1.0 g of tetrabutyl ammonium bromide and 68.5 g of aqueous dimethylamine solution having a concentration of 40%. The reactor was sealed and warmed to 130° C. The reaction was carried out under stirring for 5 hours. The reaction solution was separated to remove aqueous phase. 67.8 g of organic phase was collected. Gas chromatography detection showed that the conversion rate of p-tert-octyl phenoxy ethoxy ethyl dimethylamine was 100%, and the content thereof after concentration was 94.8%.

The above obtained p-tert-octyl phenoxy ethoxy ethyl dimethylamine was added to a 1 L four-necked reaction flask, to which were sequentially added 150.1 g of N-methylpyrrolidone and 50.0 g of benzyl chloride. The flask was heated to 203° C. to reflux. The reaction was carried out for 1.5 hours. Then, 122.0 g of cyclohexane was added slowly. The flask was cooled to carry out crystallization. 84.7 g of a white solid was collected, to obtain benzethonium chloride. The content of benzethonium chloride was 99.6% determined by titration. The measured melting point is from 159.7 to 161.0° C. As calculated with reference to p-tert-octyl phenol, an overall yield of the three steps was 76.0%.

Example 4

13.9 g of tetrabutyl ammonium chloride, 715.0 g of β,β'-dichloro diethyl ether, 300.0 g of methyl isobutyl ketone were sequentially added to a 1 L four-necked reaction flask in which 150.2 g of thymol was added. The reaction mixture was heated to 45° C. 400.0 g of sodium hydroxide solution having a concentration of 15% was slowly dropwise added. The reflux was maintained for 72 hours after the completion of the dropwise addition. The reaction solution was separated to remove aqueous phase. The organic phase was distilled under reduced pressure to separately recover methyl isobutyl ketone and excess β,β'-dichloro diethyl ether. The distillation residue was about 304.8 g of a yellow viscous liquid. Gas chromatography detection showed that the content of 5-methyl-2-isopropyl phenoxy ethoxy ethyl chloride was 96.8%.

The above product was added to a 0.5 L sealable reactor, to which were added 15.4 g of polyethylene glycol and 135.3 g of aqueous dimethylamine solution having a concentration of 40%. The reactor was sealed and warmed to 160° C. The reaction was carried out under stirring for 3 hours. The reaction solution was separated to remove aqueous phase. 251.0 g of organic phase was collected. Gas chromatography detection showed that the conversion rate of 5-methyl-2-isopropyl phenoxy ethoxy ethyl dimethylamine was 99.2%, and the content thereof after concentration was 94.8%.

The above obtained 5-methyl-2-isopropyl phenoxy ethoxy ethyl dimethylamine was added to a 1 L four-necked reaction flask, to which were sequentially added 180.0 g of trichloroethylene and 155.0 g of benzyl chloride. The flask was heated to reflux. The reaction was carried out for 4 hours. Then, 200.0 g of cyclohexane was added slowly. The flask was cooled to carry out crystallization. 292.4 g of a white solid was collected. The content of a quaternary ammonium salt of 5-methyl-2-isopropyl phenoxy ethoxy ethyl dimethylamine was 97.2% determined by titration. As calculated with reference to thymol, an overall yield of the three steps was 75.1%.

Example 5

100.0 g of polyethylene glycol 400, 84.0 g of β,β'-dichloro dibutyl ether and 200.0 g of dimethyl sulfoxide were added to a 1 L four-necked reaction flask in which 87.0 g of p-sec-butyl phenol was added. The reaction mixture was heated to 190° C. to reflux. 350.0 g of sodium hydroxide solution having a concentration of 20% was slowly dropwise added. The reflux was maintained for 1 hour after the completion of the dropwise addition. The supernatant organic phase was subjected to gas chromatography detection, which showed a conversion rate of 92.1% of p-sec-butyl phenol. Under the action of this catalyst, the reaction speed was remarkably accelerated, but with more by-product output. The reaction solution was separated to remove aqueous phase. The organic phase was distilled under reduced pressure to separately recover dimethyl sulfoxide and excess β,β'-dichloro dibutyl ether. The distillation residue was about 148.8 g of a yellow viscous liquid. Gas chromatography detection showed that the content of p-sec-butyl phenoxy butoxy butyl chloride was 67.7%, with more by-products.

The above product was added to a 1 L sealable reactor, to which were added 60.0 g of 18-crown ether-6 and 300 g of diethylamine aqueous solution having a concentration of 40%. The reactor was sealed and warmed to 200° C. The reaction was carried out under stirring for 1 hour. The reaction solution was separated to remove aqueous phase. 191.0 g of organic phase was collected. Gas chromatography detection showed that the conversion rate of p-sec-butyl phenoxy butoxy butyl diethylamine was 97.1%, and the content thereof after concentration was 62.7%.

The above obtained p-sec-butyl phenoxy butoxy butyl diethylamine was added to a 1 L four-necked reaction flask, to which were sequentially added 70.0 g of methyl isobutyl ketone and 200.0 g of benzyl chloride. The flask was heated to reflux. The reaction was carried out for 2 hours. 50.0 g of petroleum ether was added slowly. The flask was cooled to carry out crystallization. 132.0 g of a white solid was collected. As calculated with reference to p-sec-butyl phenol, an overall yield of the three steps is 56.4%.

Comparative Examples

Comparative Example 1

Synthesis of Benzethonium Chloride without Addition of a Phase Transfer Catalyst 143.0 g of β,β'-dichloro diethyl ether and 225.0 g of toluene were added to a 1 L four-necked reaction flask in which 103.0 g of p-(α,α,γ,γ-tetramethylbutyl) phenol was added. The reaction mixture was heated to reflux. 105.0 g of sodium hydroxide solution having a concentration of 20% was slowly dropwise added. The reflux was maintained for 6 hours after the completion of the dropwise addition. The supernatant organic phase was subjected to gas chromatography detection, which showed a conversion rate of 45.4% of p-tert-octyl phenol. The reaction solution was separated to remove aqueous phase. The organic phase was distilled under reduced pressure to separately recover toluene and excess β,β'-dichloro diethyl ether. The distillation residue was about 162.0 g of a yellow viscous liquid. Gas chromatography detection showed that the content of p-tert-octyl phenoxy ethoxy ethyl chloride in the liquid mixture was 43.4%.

160.0 g of p-tert-octyl phenoxy ethoxy ethyl chloride was added to a 0.5 L, sealable reactor, to which were added 135.3 g of aqueous dimethylamine solution having a concentration of 33%. The reactor was sealed and warmed to 180° C. The reaction was carried out under stirring for 4 hours. The reaction solution was separated to remove aqueous phase. 168.9 g of organic phase was collected. Gas chromatography detection showed that the conversion rate of p-tert-octyl phenoxy ethoxy ethyl dimethylamine was 40.1%, and the content thereof after concentration was 37.9%.

170.0 g of p-tert-octyl phenoxy ethoxy ethyl dimethylamine was added to a 1 L four-necked reaction flask, to which were sequentially added 100.2 g of methyl isobutyl ketone and 126.6 g of benzyl chloride. The reaction mixture was heated to reflux. The reaction was carried out for 2 hours. Then, 168.2 g of cyclohexane was added slowly. The flask was cooled to carry out crystallization. 156.8 g of a white solid was collected. The content of benzethonium chloride was 99.2% determined by titration according to the method described on page 247 of the United States Pharmacopeia USP29. The measured melting point was from 159.0 to 162.0° C. As calculated with reference to p-tert-octyl phenol, an overall yield of the three steps was less than 15%, which is remarkably far from that obtained by using a phase transfer catalyst. Thus, it does not have a practical application value.

In view of the comparison between Examples 1 to 5 and the Comparative Example, the yield of the reaction without addition of a phase transfer catalyst is very low, and it does not have a practical application value. According to the method of the present invention, a phase transfer catalyst is added during the synthesis reaction, resulting in a high yield and high purity of the product up to pharmaceutical grade.

The above is a detailed description of a method for preparation of an aryl poly(oxalkyl) quaternary ammonium compound provided by the present invention. Specific examples are described here to illustrate principle and embodiments of the present invention. The description of the above embodiments is only used to help the understanding of the method of the present invention and its core thought. It should be noted that various improvements or modifications made to the present invention by the ordinary skilled person in the relevant technical field without departing from the principle of the invention also fall within the scope of protection claimed by the claims of the present invention.

The invention claimed is:

1. A method for preparation of an aryl poly(oxalkyl) quaternary ammonium compound, said method comprising steps of:

1) reacting a phenol represented by formula (a) with a dihalopolyalkylene ether represented by formula (b) under the action of a phase transfer catalyst, to obtain an arylpoly(oxalkyl) halide represented by formula (c);

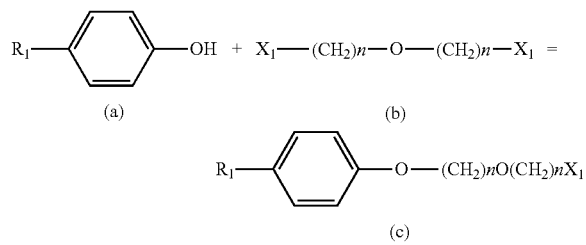

2) reacting said arylpoly(oxalkyl) halide with an amination reagent under the action of a phase transfer catalyst, to obtain an arylpoly(oxalkyl) amine represented by formula (d);

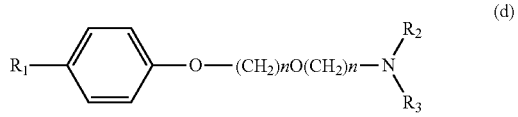

3) reacting said arylpoly(oxalkyl) amine with an alkylation reagent, to obtain an aryl poly(oxalkyl) quaternary ammonium compound represented by formula (e);

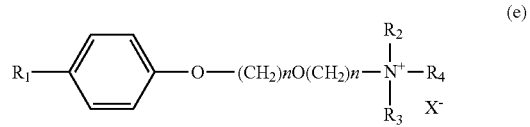

wherein, $R_1$ is H or a $C_1$ to $C_{16}$ alkyl group, located in the ortho, meta or para position; n is an integer of 2 to 6; $R_2$ is H or a $C_1$ to $C_{16}$ alkyl group; $R_3$ is H or a $C_1$ to $C_{16}$ alkyl group; $R_4$ is a $C_1$ to $C_{16}$ alkyl group; $X_1$ is Br or Cl; X is Cl, Br, or I.

2. The method according to claim 1, wherein $R_1$ is a $C_4$ to $C_{10}$ alkyl group, $R_2$ is a $C_1$ to $C_6$ alkyl group, $R_3$ is a $C_1$~$C_6$ alkyl group.

3. The method according to claim 1 or 2, wherein said phenol is one of phenol, cresol, 5-methyl-2-isopropyl phenol, 2-methyl-5-isopropyl phenol, p-tert-butyl phenol, p-sec-butyl phenol, p-tert-pentyl cresol, p-sec-octyl phenol or p-tert-octyl phenol; and said dihalopolyalkylene ether is one of β,β'-dichloro diethyl ether, β,β'-dichloro diisopropyl ether, β,β'-dichloro dibutyl ether, β,β'-dichloro dipentyl ether, β,β'-dibromo diethyl ether, β,β'-dibromo diisopropyl ether, β,β'-dibromo dibutyl ether, β,β'-dibromo dipentyl ether.

4. The method according to claim 3, wherein in step 1) a molar ratio between the phenol and the dihalopolyalkylene ether is 1:1 to 1:10.

5. The method according to claim 1 or 2, wherein said phase transfer catalyst in steps 1) and 2) is one or more of a quaternary ammonium salt, a quaternary phosphonium salt, a polyether compound, or a cyclic crown ether compound.

6. The method according to claim 5, wherein the amount of said phase transfer catalyst in step 1) is 1% to 50% of the mole number of said phenol; and the amount of said phase transfer catalyst in step 2) is 1% to 50% of the mole number of said arylpoly(oxalkyl) halide.

7. The method according to claim 6, wherein the chemical formula of said quaternary ammonium salt is formula (f), and the chemical formula of said quaternary phosphonium salt is formula (g):

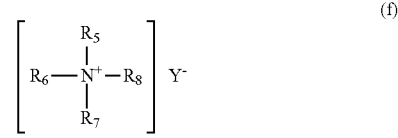

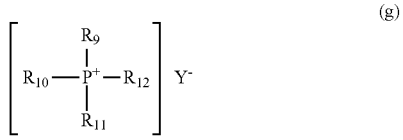

wherein each of $R_5$, $R_6$, $R_7$, $R_8$ is a $C_2$ to $C_8$ alkyl group; and each of $R_9$, $R_{10}$, $R_{11}$, $R_{12}$ is a $C_2$ to $C_8$ alkyl group; $Y^-$ is $HSO_4^-$, $Br^-$ or $Cl^-$.

8. The method according to claim 7, wherein said quaternary ammonium salt is a tetraalkyl ammonium salt or a benzyl trialkyl ammonium salt; and said quaternary phosphonium salt is a tetraalkyl phosphonium salt or a benzyl trialkyl phosphonium salt.

9. The method according to claim 8, wherein said quaternary ammonium salt is one or more of benzyl triethyl ammonium chloride, tetrabutyl ammonium chloride, tetrabutyl ammonium bromide, tetrabutyl ammonium sulfate; said quaternary phosphonium salt is methyl triphenyl phosphonium bromide; said polyether compound is one or both of a chain-like polyethylene glycol or polyethylene glycol dialkyl ethers; and said cyclic crown ether compound is one or more of 18-crown-6, 15-crown-5, cyclodextrin compound.

10. The method according to claim 1 or 2, wherein step 1) is carried out in an alkaline condition, an alkali being added is one or more of sodium amide, sodium methoxide, sodium hydroxide, potassium hydroxide, potassium carbonate; and a molar ratio between said alkali and said phenol is 1:1.0 to 1:5.0.

11. The method according to claim 1 or 2, wherein in step 1), the reaction temperature is 40° C. to 250° C., and the reaction time is 1 hour to 72 hours.

12. The method according to claim 1 or 2, wherein step 1) is carried out in organic solvent, said organic solvent is one or more of dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, butanone, methyl isobutyl ketone, methyl n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

13. The method according to claim 1 or 2, wherein said amination reagent in step 2) is one of ammonia, methylamine, dimethylamine, ethylamine, diethylamine, monoethanolamine, diethanolamine, dibenzylamine, cyclohexylamine, piperidine, morpholine.

14. The method according to claim 13, wherein in step 2), a molar ratio between said arylpoly(oxalkyl) halide and said amination reagent is 1:1.0 to 1:12.0.

15. The method according to claim 1 or 2, wherein in step 2), the reaction temperature is 40° C. to 200° C., and the reaction time is 1 hour to 48 hours.

16. The method according to claim 1 or 2, wherein said alkylation reagent in step 3) is one of benzyl chloride, benzyl bromide, p-methoxybenzyl chloride, 2-methyl-1-allyl chloride, iodomethane, bromoethane.

17. The method according to claim 16, wherein in step 3), a molar ratio between said arylpoly(oxalkyl) amine and the alkylation reagent is 1:1 to 1:10.

18. The method according to claim 1 or 2, wherein in step 3), the reaction temperature is 40° C. to 250° C., and the reaction time is 1 hour to 48 hours.

19. The method according to claim 1 or 2, wherein step 3) is carried out in organic solvent, said organic solvent is halogenated hydrocarbons, ketones, ethers containing from 2 to 8 carbon atoms and aromatic hydrocarbons, specifically, one or more of butanone, methyl isobutyl ketone, methyl-n-butyl ketone, methyl tert-butyl ketone, methyl isoamyl ketone, ethyl isobutyl ketone, ethyl n-butyl ketone, ethyl tert-butyl ketone, ethyl isoamyl ketone, 2-hexanone, 3-hexanone, diethyl ketone, cyclohexanone, cyclopentanone, dimethyl sulfoxide, methyl ethyl sulfoxide, N,N-dimethyl formamide, N,N-dimethyl acetamide, diethyl formamide, dipropylene glycol dimethyl ether, dipropylene glycol diethyl ether, diethylene glycol dimethyl ether, diethylene glycol diethyl ether, ethylene glycol monomethyl ether, ethylene glycol monoethyl ether, ethylene glycol dimethyl ether, ethylene glycol diethyl ether, trichloroethylene, trichloroethane, dichloroethane, chloroform, carbon tetrachloride, N-methyl pyrrolidone, tetrahydrofuran, toluene, xylene, ethylbenzene, ethyl acetate, propyl acetate, butyl acetate.

20. The method according to claim 1 or 2, wherein a crystallization solvent is used in step 3), said crystallization solvent is one or more of carbon disulfide, isopropyl ether, petroleum ether, cyclohexane.

\* \* \* \* \*